(12) United States Patent
Anderson

(10) Patent No.: US 7,377,179 B2
(45) Date of Patent: May 27, 2008

(54) SYSTEM, METHOD, AND APPARATUS FOR WIRELESS NON-POWERED STRESS HISTORY AND FATIGUE MONITORING OF A STRUCTURE

(75) Inventor: Todd Anderson, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 200 days.

(21) Appl. No.: 11/273,460

(22) Filed: Nov. 14, 2005

(65) Prior Publication Data

US 2007/0107530 A1    May 17, 2007

(51) Int. Cl.
*G01L 1/18* (2006.01)
*G01R 33/18* (2006.01)

(52) U.S. Cl. .................. 73/767; 73/787; 702/34; 324/209

(58) Field of Classification Search ............. 73/808, 73/763, 767–769, 775–779, 786–787, 802; 324/209, 228, 234–243; 702/33–34
See application file for complete search history.

(56) References Cited

U.S. PATENT DOCUMENTS

| | | | |
|---|---|---|---|
| 4,433,581 A | 2/1984 | Scott et al. | 73/786 |
| 5,520,055 A | 5/1996 | Füssinger | 73/762 |
| 5,531,123 A | 7/1996 | Henkel | 73/795 |
| 6,014,896 A | 1/2000 | Schoess | 73/583 |
| 6,768,312 B2 * | 7/2004 | Sun et al. | 324/525 |
| 6,928,881 B2 | 8/2005 | Brennan | 714/22 |
| 7,024,315 B2 * | 4/2006 | Giurgiutiu | 702/33 |
| 7,034,661 B2 * | 4/2006 | Lonsdale et al. | 340/10.41 |
| 7,117,742 B2 * | 10/2006 | Kim | 73/587 |
| 7,174,255 B2 * | 2/2007 | Giurgiutiu et al. | 702/35 |
| 2002/0154029 A1 * | 10/2002 | Watters et al. | 340/870.07 |
| 2004/0078662 A1 | 4/2004 | Hamel et al. | 714/22 |
| 2005/0114045 A1 * | 5/2005 | Giurgiutiu et al. | 702/35 |
| 2007/0095160 A1 * | 5/2007 | Georgeson et al. | 73/866 |

FOREIGN PATENT DOCUMENTS

JP    92004061347    2/2004

OTHER PUBLICATIONS

Cain et al. "Degradation of Piezoelectric Materials" NPL Report CMMT (A) 148; Jan. 1999.*
Lowrie et al. "Time Dependent Behaviour of Piezo-Electric Materials" NPL Report CMMT(A) 151. Mar. 1999.*

* cited by examiner

*Primary Examiner*—Edward Lefkowitz
*Assistant Examiner*—Jonathan Dunlap
(74) *Attorney, Agent, or Firm*—Bracewell & Giuliani LLP

(57) ABSTRACT

A wireless, non-powered fatigue monitoring sensor uses a piezoelectric element that is attached to the surface of or embedded within a structure to be monitored. When subjected to stress over time, the material properties of the element change reliably and permanently. These properties are used to determine the fatigue history of the structure. The monitoring device requires no power for monitoring and is nondestructively queried to determine the stress history using wireless means such as radio frequency technology.

24 Claims, 3 Drawing Sheets

SYSTEM, METHOD, AND APPARATUS FOR WIRELESS NON-POWERED STRESS HISTORY AND FATIGUE MONITORING OF A STRUCTURE

BACKGROUND OF THE INVENTION

1. Technical Field

The present invention relates in general to monitoring stress in a structure and, in particular, to an improved system, method, and apparatus for a wireless, non-powered stress history and fatigue monitoring of a structure.

2. Description of the Related Art

Many structures, especially in the aerospace industry, must be monitored over time for overload and/or fatigue damage. Typically, this is done in one of two ways. First, a structure may be statistically evaluated for stress or fatigue. With this method the exact number of cycles is not known, but it does offer a prediction of what is typical for a certain amount of running time or flights. Second, active strain gages and/or accelerometers, for example, may be used to count cycles. Unfortunately, the first method is approximate, while the second method is costly and not feasible for most in-service applications due to wiring and power requirements. Some practitioners have proposed "power harvesting" for such applications whereby energy is harvested from vibrations, solar, RF, thermal, or other power sources. Although that solution would eliminate the power wiring requirements or batteries, the proposition is very challenging for continuous operation while a structure is in service.

Examples of externally powered prior art solutions include U.S. Pat. No. 4,433,581 to Scott, which describes strain gages that are powered by conventional means. U.S. Pat. No. 5,520,055 to Fussinger shows a device that has notches that break upon a sufficient number of cycles of fatigue. U.S. Pat. No. 5,531,123 to Henkel uses a fatigue monitor that must be physically removed from the underlying structure and then inspected by viewing striations formed in the monitor due to the fatigue. U.S. Pat. No. 6,014,896 to Schoess discloses a piezoelectric device that emits an acoustic wave and is battery powered. U.S. Pat. No. 6,928,881 to Brennan discloses a power detector with strain gages and a memory device with data storage. Finally, U.S. Patent Application No. 20040078662 to Hamel describes the energy harvesting concept for wireless sensors. Although each of these designs is workable, an improved solution for monitoring the fatigue of components while they are in service and can remain in service after inspection would be desirable.

SUMMARY OF THE INVENTION

One embodiment of a system, method, and apparatus for a wireless, non-powered, non-destructive fatigue monitoring sensor is disclosed. The present invention comprises, for example, a piezoelectric element that is attached to the surface of or embedded within a structure to be monitored. When subjected to stress over time, the electromechanical properties of the element change reliably and permanently. The change in these properties is then used to determine the fatigue history of the structure. The monitoring device requires no power for monitoring and is queried to determine the stress history using wireless means such as radio frequency (RF) technology. Moreover, the monitoring device is not required to be removed from the underlying structure.

In one embodiment, the sensor element is bonded to the surface of the structure being monitored. Before service, the electromechanical behavior of the element is calibrated. This behavior may be measured by, for example, its piezoelectric properties, components and/or magnitude of the admittance or impedance, or by its piezoelectric coupling. Once recorded, the structure is put into service and subjected to cycles of stress. When loaded, the electromechanical properties of the monitoring device degrade, thus changing its measured characteristics (e.g., impedance, admittance, etc.). High stresses produce a large change and provide a measure of overload. Time at elevated stress also degrades the properties and provides a measure of fatigue.

After a period of service, the material is queried to measure its new electromechanical properties by a remotely powered device, such as an RF circuit. The change in these properties is related to the stress history of the monitoring element and, therefore, the host structure. With the stress history known, a prediction of residual life is determined. In addition, multiple piezoelectric elements that are tuned to respond to different stress levels can be attached to the host structure to provide better stress history fidelity.

The foregoing and other objects and advantages of the present invention will be apparent to those skilled in the art, in view of the following detailed description of the present invention, taken in conjunction with the appended claims and the accompanying drawings.

BRIEF DESCRIPTION OF THE DRAWINGS

So that the manner in which the features and advantages of the invention, as well as others which will become apparent are attained and can be understood in more detail, more particular description of the invention briefly summarized above may be had by reference to the embodiment thereof which is illustrated in the appended drawings, which drawings form a part of this specification. It is to be noted, however, that the drawings illustrate only an embodiment of the invention and therefore are not to be considered limiting of its scope as the invention may admit to other equally effective embodiments.

DETAILED DESCRIPTION OF THE INVENTION

Piezoelectric materials have time-dependent properties that may be employed for use by monitoring them as degradation mechanisms. For example, with respect to aging, there is a loss in mobility of the domain walls as they become pinned by structural inhomogeneities (e.g., pores and cracks) and charge carriers (e.g., vacancies and dopants). Above a certain field strength, domain wall movement can occur. Degradation starts above this threshold and increases with field due to more extensive domain wall motion. With regard to stress level, the degradation also occurs in a similar fashion as that under high field strength as the domain walls are unable to respond quickly at higher frequencies. Thus, the aging rate is less than at lower frequencies. Depoling involves the net polarization direction of the material with respect to the poled direction being lost, because the domains "switch" (i.e., change their orientation) to become more random. Depoling is affected by temperature, stress, and field. In addition, microcracking and failure of electrode/ceramic interface may be evaluated as a degradation mechanism.

Figure 1:
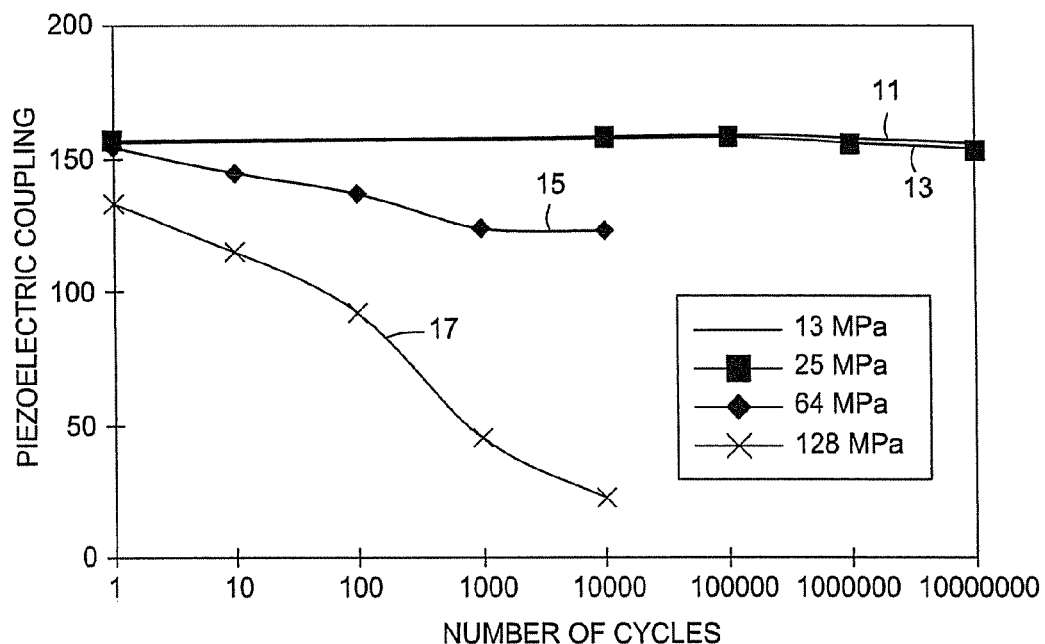
FIG. 1 illustrates plots of a time-dependent property of a material over different stress ranges and mechanical cycles.

For example, FIG. 1 depicts various plots that illustrate a time-dependent, piezoelectric property of a material over different stress ranges and mechanical cycles. The material selected may comprise a piezoelectric (e.g., ferroelectric) material. At a stress level plot 11 at 13 MPa, almost negligible degradation of the material property is observed. The same is true for stress level plot 13 at 25 MPa. However, at plots 15, 17 at 64 MPa and 128 MPa, respectively, a significant degradation of the property is observed.

Figure 2:
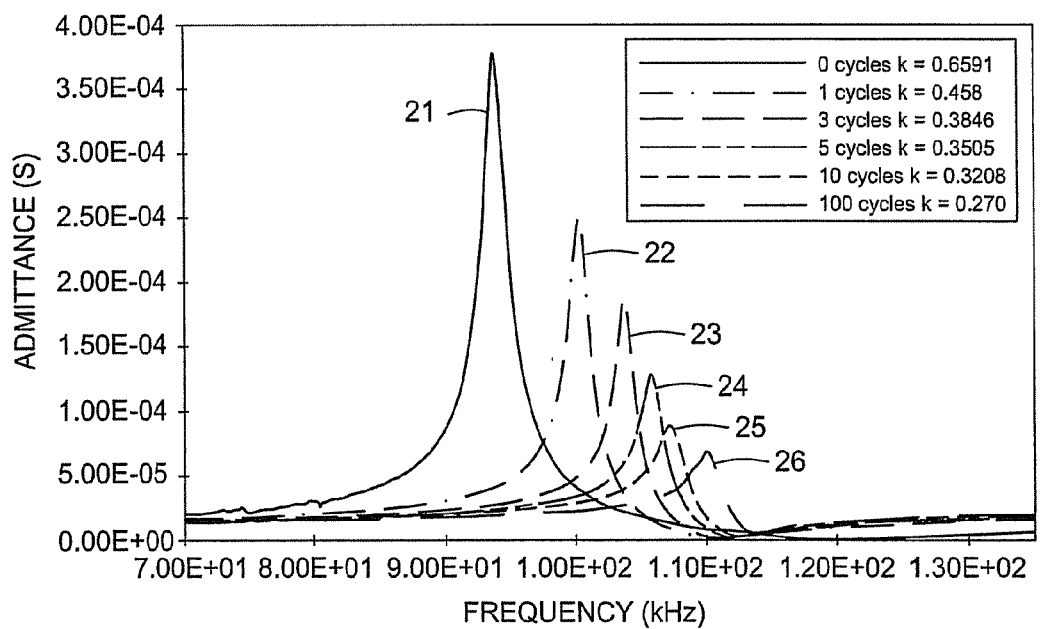
FIG. 2 illustrates plots of a time-dependent admittance property of a material after various mechanical cycles at constant stress.

Another example of the degradation characteristic is depicted in FIG. 2. A series of plots 21-26 illustrate the time-dependent admittance property of a material as a function of frequency after various mechanical cycles at constant stress. At zero cycles, the baseline response of the material is captured by plot 21. As the number of cycles at constant amplitude stress in the material accumulates, the peak admittance of the sensor element degrades as depicted by plots 22-26. As presented in the figure legend, the piezoelectric coupling ratio "k" also degrades as a function of the number of cycles. Either of these quantities can be related to the fatigue history of the structural element.

Figure 3:
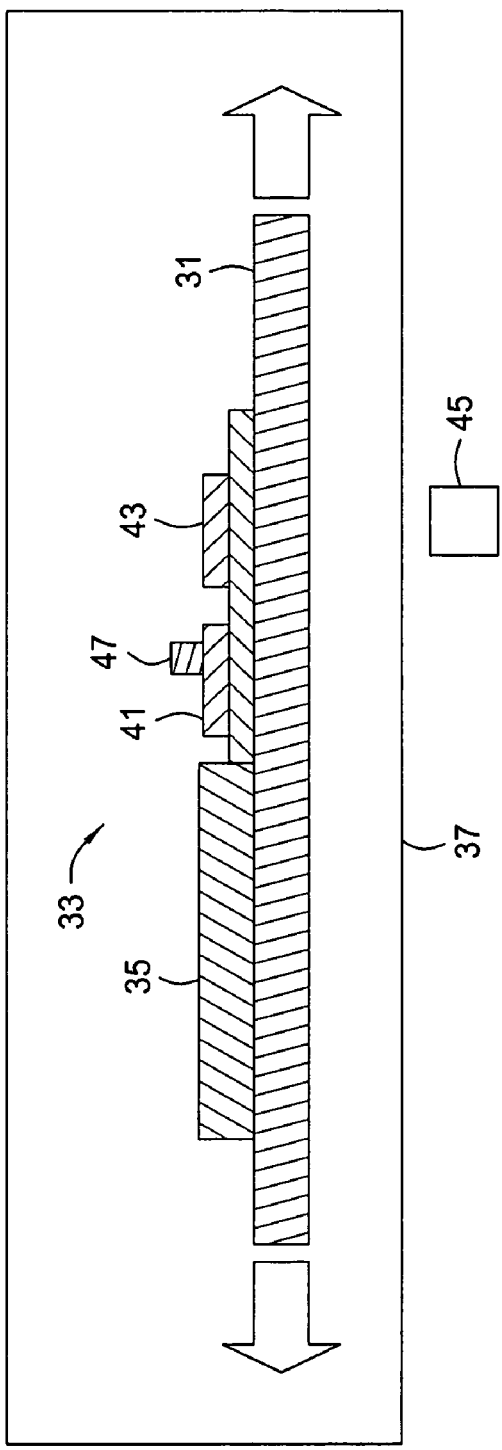
FIG. 3 is a schematic side view of one embodiment of a device mounted to a structure and is constructed in accordance with the present invention.

Referring now to FIG. 3, one embodiment of an apparatus and system for analyzing structural stress and/or monitoring fatigue history of a structure is shown. A structure 31 such as, for example, a wing skin, a spar, a rib, an engine cowling, etc., is monitored over time to assess its on-going service life and determine whether it is in need of repair or replacement. A device 33 having an element 35 is mounted to the structure 31. In the embodiment shown, the structure 31 forms a portion of a component 37 (e.g., an aircraft). In this version, the device 33 is mounted inside the component 37 such that the device 33 (and element 35) are physically inaccessible from an exterior of the component 37.

The element 35 of device 33 may comprise, for example, a piezoelectric element, and has a material property that degrades over time due to stress cycling of the structure 31 during service operation of the structure 31. The property may comprise an electromechanically coupled property such as impedance, admittance, piezo strain coefficients, piezo coupling, and complex portions of the impedance or admittance. The element 35 may comprise, for example, a thin film, a sheet, a beam, or a rod, and may be, for example, bonded to the structure 31 or embedded inside the structure 31.

A sensor 41 is coupled to the element 35 for detecting a condition of the property of the element 35. No portion of device 33, including the sensor 41 and the element 35 have an internal source of power. Alternatively, an internal power source, such as a battery, may be provided depending on the application. In one embodiment, the sensor 41 comprises an impedance analyzer that scans a frequency range with respect to the element 35, an antenna 43 for enhancing communication with a detector 45, and a microprocessor 47 for controlling the sensor 41. The detector 45 provides wireless power to and wirelessly communicates with the sensor 41 to detect the condition of the property of the element 35 and thereby ascertain a level of fatigue and prediction of residual life of the structure 31. As loads are applied over time to the structure 31, stress and strain are generated. In effect, the load history of the structure 31 also is monitored. In the embodiment shown, the detector 45 is non-invasive, non-destructive, and remote relative to the element 35 and the sensor 41. For example, the sensor 41 may be inductively powered by the detector 45 and use radio frequency to communicate with the sensor 41.

Figure 4:
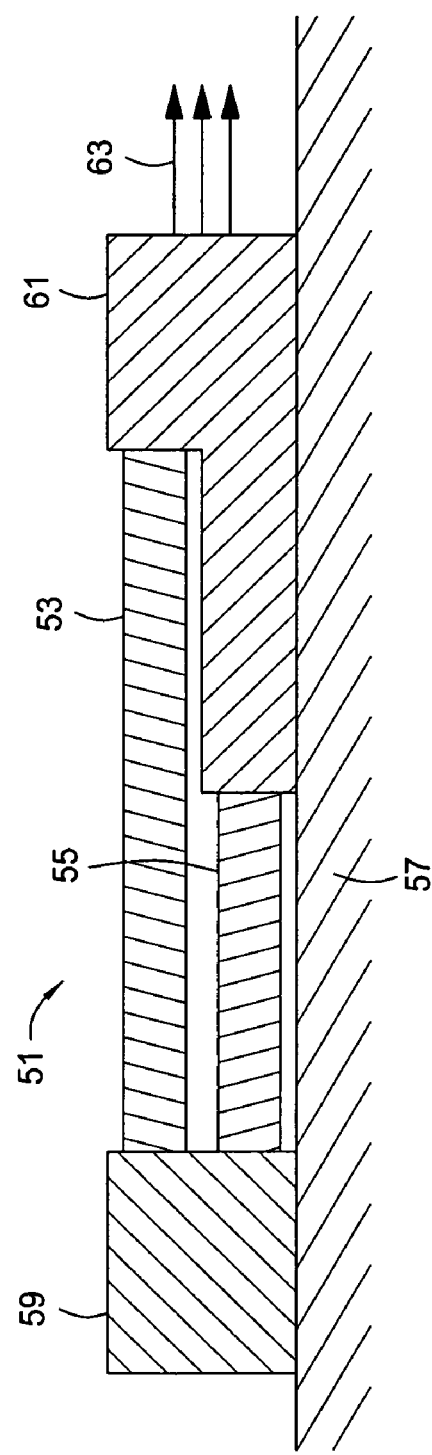
FIG. 4 is a schematic side view of another embodiment of a device mounted to a structure and is constructed in accordance with the present invention.

Referring now to FIG. 4, another embodiment of a device 51 constructed in accordance with the present invention is shown. For simplicity other components, such as the sensor, antenna, and microprocessor, are not shown. In this version, the element comprises a plurality of elements 53, 55. Although only two elements are shown, many more elements may be used depending on the application. Each element 53, 55 has a different physical property than the others to increase a fidelity and sensitivity to fatigue cycle prediction of the structure 57.

In the embodiment shown, a first fixture 59 is secured to the structure 57. A second fixture 61 is mounted to the structure 57, spaced apart from the first fixture 59 and displaceable relative to the first fixture 59. The elements 53, 55 extend between the first and second fixtures 59, 61. As structure 57 (and, thus, device 51) experience stress during operational service of structure 57, the elements 53, 55 and second fixture 61 are displaced in length (see arrows 63). One of the elements 53, 55 is sensitive to low stresses, and another one of the elements 53, 55 is sensitive to high stresses. For example, element 53 may have a fatigue life of 0 to 10,000 cycles, and element 55 may have a fatigue life of 50,000 cycles. In this way the fidelity of the measurements monitored by the detector (described above) is improved. Device 51 and its system otherwise operates in the same manner and has the same advantages as described above for device 33 and its system.

Figure 5:
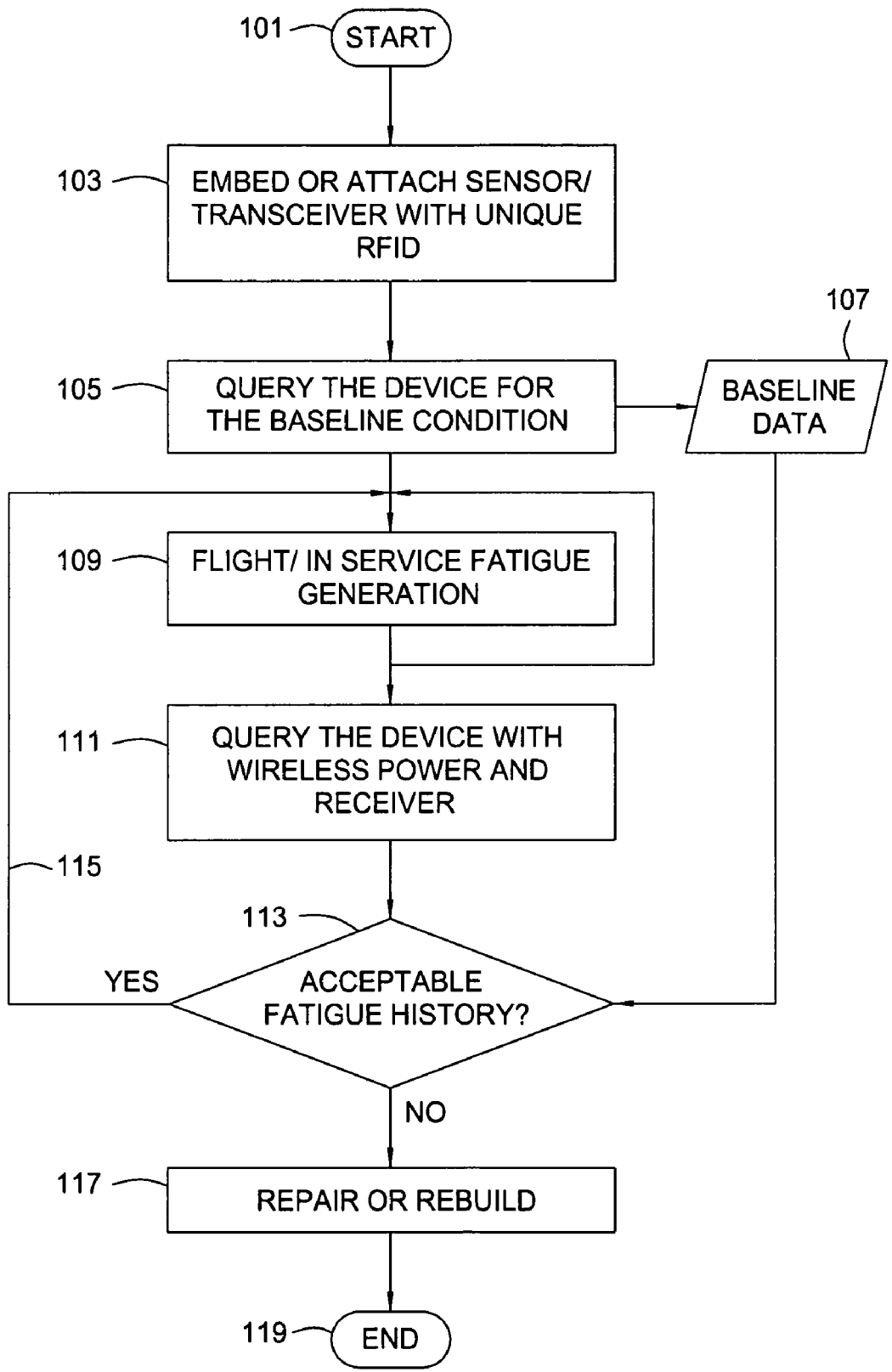
FIG. 5 is one embodiment of a method constructed in accordance with the present invention.

The present invention also comprises a method of monitoring structural stress. In one embodiment (FIG. 5), the method begins as indicated at step 101, and comprises mounting a device (e.g., with a unique radio frequency identifier) to a structure (step 103); querying the device for a baseline condition of the device (step 105); saving the baseline condition (step 107); placing the structure in service such that the structure and device experience stress cycles (step 109); querying the device after a period of service (step 111); determining whether the device and, therefore, the structure have an acceptable fatigue history (step 113); continuing service of the structure if the fatigue history is acceptable (step 115); and discontinuing service of the structure if the fatigue history is unacceptable (step 117); before ending as indicated at step 119.

Alternatively, step 103 may comprise bonding the device to a surface of the structure or embedding the device inside the structure. Steps 105, 111 may be performed wirelessly, non-intrusively, non-destructively, and remotely, and may be performed without providing the device with a power source such that wireless power is provided to the device from an external source. Step 109 may comprise degrading a property of the device over time due to stress cycling of the structure during service.

In addition, the method may further comprise providing the device with a piezoelectric element and monitoring a property of the piezoelectric element; inductively powering the device and using radio frequency to communicate with the device; and/or increasing a fidelity and sensitivity to fatigue cycle prediction of the structure via different physical properties of the device. Moreover, step 117 may comprise repairing or rebuilding the structure.

The present invention has several advantages, including no requirement for power to record the stress history of the host structure. The query to determine fatigue of the structure is externally powered and has an external control circuit so that the structure is wirelessly investigated for measurements and communications by using, for example, RF power harvesting to power the circuit that measures and transmits the new electromechanical properties of the monitoring element. In addition, the monitoring element may be scaled down to micro-electromechanical systems (MEMS) for minimal intrusiveness. The multiple elements embodiment may be used to tune the device to respond to different stress histories of the host structure while making the device sensitive to a larger range of stresses and cycles.

While the invention has been shown or described in only some of its forms, it should be apparent to those skilled in the art that it is not so limited, but is susceptible to various changes without departing from the scope of the invention.

What is claimed is:

1. An apparatus for analyzing stress, comprising:
    an element adapted to be mounted to a structure, the element having a material property that degrades over time due to stress cycling of the structure during service operation of the structure;
    a sensor coupled to the element for detecting a condition of the property of the element, and neither the sensor nor the element have a source of power;
    a detector for providing wireless power to and wirelessly communicating with the sensor to detect the condition of the property of the element and adapted to ascertain a level of fatigue and prediction of residual life of the structure, the detector being non-invasive, non-destructive, and remote relative to the element and the sensor; wherein
    the element comprises a plurality of elements, each of which has a different physical property than other ones of the elements to increase a fidelity and sensitivity to fatigue cycle prediction of the structure; and wherein a first fixture is secured to the structure, a second fixture is mounted to the structure, spaced apart from the first fixture and displaceable relative to the first fixture, and the plurality of elements extend between the first and second fixtures, and the physical property is length.

2. An apparatus according to claim 1, wherein the element comprises a piezoelectric element and the material property of the element is selected from the group consisting of impedance, admittance, piezo strain coefficients, piezo coupling, and complex portions of the impedance or admittance.

3. An apparatus according to claim 1, wherein the sensor is inductively powered by the detector and uses radio frequency to communicate with the sensor.

4. An apparatus according to claim 1, wherein the sensor comprises an impedance analyzer that scans a frequency range with respect to the element, an antenna for enhancing communication with the detector, and a microprocessor for controlling the sensor.

5. An apparatus according to claim 1, wherein the structure forms a portion of a component and the element is mounted inside the component such that the element is physically inaccessible from an exterior of the component.

6. An apparatus according to claim 1, wherein the element comprises a form selected from the group consisting of a thin film, a sheet, a beam, and a rod, and wherein a means of mounting the element to the structure is selected from the group consisting of bonding the element to the structure and embedding the element in the structure.

7. An apparatus according to claim 1, wherein one of the plurality of elements is sensitive to low stresses, and another one of the plurality of elements is sensitive to high stresses.

8. A system for analyzing structural stress, comprising:
    a structure;
    an element mounted to the structure, the element having a material property that degrades over time due to stress cycling of the structure during service operation of the structure;
    a sensor coupled to the element for detecting a condition of the material property of the element, and neither the sensor nor the element have a source of power; and
    a detector for providing wireless power to and wirelessly communicating with the sensor to detect the condition of the material property of the element and thereby ascertain a level of fatigue and prediction of residual life of the structure, the detector being non-invasive, non-destructive, and remote relative to the element and the sensor; and wherein
    the element comprises a plurality of elements, each of which has a different physical property than other ones of the elements to increase a fidelity and sensitivity to fatigue cycle prediction of the structure; and wherein a first fixture is secured to the structure, a second fixture is mounted to the structure, spaced apart from the first structure and displaceable relative to the first fixture, and the plurality of elements extend between the first and second fixtures and the physical property is length.

9. A system according to claim 8, wherein the element comprises a piezoelectric element and the material property of the element is selected from the group consisting of impedance, admittance, piezo strain coefficients, piezo coupling, and complex portions of the impedance or admittance, and wherein the sensor is inductively powered by the detector and uses radio frequency to communicate with the sensor.

10. A system according to claim 8, wherein the sensor comprises an impedance analyzer that scans a frequency range with respect to the element, an antenna for enhancing communication with the detector, and a microprocessor for controlling the sensor.

11. A system according to claim 8, wherein the structure forms a portion of a component and the element is mounted inside the component such that the element is physically inaccessible from an exterior of the component.

12. A system according to claim 8, wherein the element comprises a form selected from the group consisting of a thin film, a sheet, a beam, and a rod, and wherein a means of mounting the element to the structure is selected from the group consisting of bonding the element to the structure and embedding the element in the structure.

13. A system according to claim 8, wherein one of the plurality of elements is sensitive to low stresses, and another one of the plurality of elements is sensitive to high stresses.

14. An apparatus for analyzing stress, comprising:
    a plurality of elements adapted to be mounted to a structure, each of the elements having a different property than other ones of the elements to increase a fidelity and sensitivity to fatigue cycle prediction of the structure, wherein one of the plurality of elements is sensitive to low stresses, and another one of the plurality of elements is sensitive to high stresses, and the properties degrade over time due to stress cycling of the structure during service operation of the structure;

a sensor coupled to each of the elements for detecting a condition of the property of a respective one of the elements, and neither the sensors nor the elements have a source of power; and a detector for providing wireless power to and wirelessly communicating with the sensors to detect the condition of the properties of the elements and adapted to ascertain a level of fatigue and prediction of residual life of the structure, the detector being non-invasive, non-destructive, and remote relative to the elements and the sensors.

15. An apparatus according to claim 14, wherein the elements comprise piezoelectric elements and the properties of the elements are selected from the group consisting of impedance, admittance, piezo strain coefficients, piezo coupling, and complex portions of the impedance or admittance.

16. An apparatus according to claim 14, wherein the sensors are inductively powered by the detector which uses radio frequency to communicate with the sensors.

17. An apparatus according to claim 14, wherein the sensors comprise impedance analyzers that scan a frequency range with respect to the elements, antennas for enhancing communication with the detector, and microprocessors for controlling respective ones of the sensors.

18. An apparatus according to claim 14, wherein the structure forms a portion of a component and the elements are mounted inside the component such that the elements are physically inaccessible from an exterior of the component.

19. An apparatus according to claim 14, wherein the elements comprise a form selected from the group consisting of a thin film, a sheet, a beam, and a rod, and wherein a means of mounting the elements to the structure is selected from the group consisting of bonding the elements to the structure and embedding the elements in the structure.

20. A system for analyzing structural stress, comprising:
a structure;
a plurality of elements mounted to the structure, each of which has a different length to increase a fidelity and sensitivity to fatigue cycle prediction of the structure, and the lengths change over time due to stress cycling of the structure during service operation of the structure;

a first fixture is secured to the structure;

a second fixture mounted to the structure, spaced apart from the first fixture and displaceable relative to the first fixture, and the plurality of elements extend between the first and second fixtures;

a sensor coupled to each of the elements for detecting a condition of the lengths of the elements, and neither the sensors nor the elements have a source of power; and a detector for providing wireless power to and wirelessly communicating with the sensors to detect the condition of the lengths of the elements and thereby ascertain a level of fatigue and prediction of residual life of the structure, the detector being non-invasive, non-destructive, and remote relative to the elements and the sensors.

21. A system according to claim 20, wherein the elements comprise piezoelectric elements and material properties of the elements are selected from the group consisting of impedance, admittance, piezo strain coefficients, piezo coupling, and complex portions of the impedance or admittance, and wherein the sensors are inductively powered by the detector which uses radio frequency to communicate with the sensors.

22. A system according to claim 20, wherein the sensors comprise impedance analyzers that scan a frequency range with respect to the elements, antennas for enhancing communication with the detector, and microprocessors for controlling respective ones of the sensors.

23. A system according to claim 20, wherein the structure forms a portion of a component and the elements are mounted inside the component such that the elements are physically inaccessible from an exterior of the component.

24. A system according to claim 20, wherein the elements comprise a form selected from the group consisting of a thin film, a sheet, a beam, and a rod, and wherein a means of mounting the elements to the structure is selected from the group consisting of bonding the elements to the structure and embedding the elements in the structure.

* * * * *

UNITED STATES PATENT AND TRADEMARK OFFICE
CERTIFICATE OF CORRECTION

PATENT NO. : 7,377,179 B2
APPLICATION NO. : 11/273460
DATED : May 27, 2008
INVENTOR(S) : Todd Anderson It is certified that error appears in the above-identified patent and that said Letters Patent is hereby corrected as shown below:

On the Title Page Item (73):

Delete:

"Assignee: General Electric Company
            Schenectady, NY (US)"

and

Insert:

Item --(73) Assignee: Lockheed Martin Corporation
                      Bethesda, Maryland (US)--

Signed and Sealed this

Tenth Day of November, 2009

David J. Kappos
*Director of the United States Patent and Trademark Office*